United States Patent [19]

Bender

[11] 4,446,132

[45] May 1, 1984

[54] NONTOXIC ASPIRIN COMPOSITION

[75] Inventor: Audrey L. Bender, Huntington Valley, Pa.

[73] Assignee: Dynatech Laboratories Incorporated, Alexandria, Va.

[21] Appl. No.: 357,074

[22] Filed: Mar. 11, 1982

[51] Int. Cl.$^3$ .................... A61K 31/61; A61K 31/615
[52] U.S. Cl. .................................... 424/233; 424/234
[58] Field of Search ................................ 424/233, 234

[56] References Cited

U.S. PATENT DOCUMENTS 2,101,807  12/1937  Miller et al. ..................... 424/233

Primary Examiner—Stanley J. Friedman
Attorney, Agent, or Firm—LeBlanc, Nolan, Shur & Nies

[57] ABSTRACT

An analgesic aspirin composition having acetylsalicylic acid and glycine in an amount equal to at least approximately 33.3% of the weight of the acetylsalicylic acid for rendering the aspirin nontoxic.

7 Claims, No Drawings

NONTOXIC ASPIRIN COMPOSITION

This invention relates to the compounding of the analgesic acetylsalicylic acid (aspirin).

Pure acetylsalicylic acid (aspirin) has been the most commonly used medication since its introduction many years ago. It has been regarded by the public as the thing nearest to a completely safe drug available on the market.

While aspirin taken occasionally in limited dosages is relatively safe, it has certain disadvantages. It has a bitter taste, so that it is generally taken in the form of pills rather than in solution or as a powder. Moreover, when used regularly, it has undesirable side effects which limit its utility. Where massive dosages are needed, as in the case of chronic arthritis, these side effects—generally known as salicylate poisoning—often limit the dosages to a level at which they are no longer effective. In many cases, particularly where a patient has an underlying mild-to-moderate chronic atrophic gastritis, aspirin aggravates the condition to cause the gastritis to become hemorrhagic. This effect also seems to be due to the conversion of the aspirin to salicylic acid salts, and is related to the appearance of salicylates in the blood stream.

It has been proposed (U.S. Pat. No. 2,933,821) to combine aspirin with lysine in order to overcome its bitter taste, and produce an aspirin composition without the characteristic bitter taste of aspirin. However, this combination has no effect on the toxic side effects of aspirin—it still degrades to the salicylic acid in vivo, and the salicylates which appear in the blood stream have the same toxic effects as with unblended aspirin.

I have found that acetylsalicylic acid, when combined with 33.3% to 222% of its weight of glycine, not only loses its bitter taste, but also is prevented from breaking down into salicylates in the stomach, so that the common toxic side effects of aspirin are overcome.

This invention is based on my discovery that glycine suppresses the in vivo breakdown of acetylsalicylic acid to salicylic acid and its salts if glycine is mixed with acetyl-salicylic acid in an amount at least equal to approximately 33.3% of the weight of the acetylsalicylic acid that is present in the composition and preferably in an amount equal to approximately 55.6% of the weight of the acetylsalicylic acid. For an analgesic aspirin composition containing 90% by weight of acetylsalicylic acid and 10% by weight of starch, the amount of glycine used is equal to at least 30% of the weight of the aspirin composition and is preferably present in an amount equal to 50% of the aspirin composition. I may use more glycine without impairing the therapeutic effect of the aspirin, but for cost reasons, I prefer not to use glycine in an amount in excess of approximately 200% of the weight of the 90% pure aspirin composition mentioned above. Mixing glycine with the acetylsalicylic acid in an amount at least approximately equal to 33.3% of the weight of the acetylsalicylic acid which is present in the composition is sufficient to substantially suppress the in vivo breakdown of the acetylsalicylic acid into salicylic acid and its salts without impairing the therapeutic effect of acetylsalicylic acid.

In addition to the inert materials normally present in the aspirin tablets, I may add small amounts of taste-improving additives, such as, for example, mannitol, sugars, and various flavoring agents. The pH can be adjusted close to the neutral point to produce an aspirin pill which can not only be swallowed whole but which can be sucked, chewed, or allowed to dissolve sublingually.

Extensive clinical testing of the medication over a period of time indicates that the medication of this invention is as effective as ordinary aspirin in relieving pain. A group of fifty patients, ranging in age from 5 to 76, was treated with 5 gr aspirin tablets having the following composition, based on the total weight of the formulation:

aspirin composition (containing 90% by weight of acetylsalicylic acid and 10% by weight of starch)—64.6%;
glycine (amino acetic acid)—31.3%;
sodium saccharin—0.4%;
sodium cyclamate—3.6%; and
lemon flavor (FLAVO-LOCK)—0.1%.

In general, young children preferred a sweeter-tasting product; pain was relieved in most cases, but not in all, as in a similar group of control patients tested with ordinary aspirin. Significantly, of the group treated with my medication there were five patients with records of gastritis, or stomach or intestinal ulcers, all of whom suffered upset stomachs or bleeding under aspirin therapy. None of them reported any such symptoms when treated with the above composition.

In place of sodium saccharin, a like amount of sodium cyclamate may be used in the above composition, making the total amount of sodium cyclamate present equal to 4.0% of the total weight of the composition. Alternatively, the sodium cyclamate may be replaced with a like amount of sodium saccharin in the above composition, making the total amount of sodium saccharin present equal to 4.0% of the total weight of the composition.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description; and all changes which come within the meaning and range of equivalency of the claims are therefore intended to be embraced therein.

What is claimed and desired to be secured by Letters Patent is:

1. A method of treating headaches and other disorders normally treated with aspirin, comprising the steps of providing an admixture comprising acetylsalicylic acid and glycine in water-free dosage form in which the glycine is unreacted with said acid, and orally administering the dosage form of said admixture while the glycine is still unreacted with said acid, the unreacted glycine in the administered admixture being present in an amount sufficient to suppress the in vivo breakdown of said acid in the acidic environment of the human stomach without substantially impairing the therapeutic effect of the acetylsalicylic acid.

2. The method defined in claim 1 wherein the amount of glycine present in said admixture is equal to at least one-third of the weight of the acetylsalicylic acid.

3. The method defined in claim 1 wherein the amount of glycine present in said admixture is equal to approximately 55% of the weight of the acetylsalicylic acid in the admixture.

4. The method defined in claim 1 wherein the dosage form of said admixture is a tablet form.

5. The method defined in claim 4 wherein said admixture includes a quantity of starch mixed with the glycine and the acetylsalicylic acid.

6. A method of treating headaches and other disorders normally treated with aspirin, comprising the steps of mixing glycine with acetylsalicylic acid to provide a water-free orally ingestible admixture without reacting said glycine with said acid, providing said admixture in water-free dosage form which is ready for swallowing without reacting the glycine with the acetylsalicylic acid so that the glycine is still unreacted with said acid upon swallowing the admixture, and orally administering the dosage form of said admixture, the unreacted glycine in the administered admixture being present in an amount sufficient to suppress the in vivo breakdown of said acetylsalicylic acid to salicylic acid and its salts in the human stomach for enabling the admixture to pass through the human stomach before breakdown of the acetylsalicylic acid without substantially impairing the therapeutic effect of said acetylsalicylic acid.

7. A method of treating headaches and other disorders normally treated with aspirin, comprising the steps of mixing at least approximately 33 parts by weight of glycine with 100 parts by weight of acetylsalicylic acid to provide a water-free orally ingestible admixture without reacting said glycine with said acid, providing said admixture in water-free dosage form which is ready for swallowing without reacting the glycine with the acetylsalicylic acid so that the glycine is still unreacted with said acid upon swallowing the admixture, and orally administering the dosage form of said admixture, the unreacted glycine in said admixture being present in an amount sufficient to render said admixture non-acid soluble in the acidic environment of the human stomach and to thereby suppress the in vivo breakdown of said acetylsalicylic acid to salicylic acid and its salts in the human stomach for enabling the admixture to pass through the human stomach before breakdown of the acetylsalicylic acid without substantially impairing the therapeutic effect of said acetylsalicylic acid.

* * * * *

UNITED STATES PATENT AND TRADEMARK OFFICE
CERTIFICATE OF CORRECTION

PATENT NO. : 4,446,132

DATED : May 1, 1984

INVENTOR(S) : Audrey L. Bender

It is certified that error appears in the above-identified patent and that said Letters Patent is hereby corrected as shown below:

On the title page:

Name of inventor should be changed to read:

--Audrey L. Bender, Executrix of Estate of Charles E. Bender, Deceased--

Signed and Sealed this

Twenty-first Day of May 1985

[SEAL]

Attest:

DONALD J. QUIGG

*Attesting Officer*  *Acting Commissioner of Patents and Trademarks*